United States Patent
Einig et al.

(10) Patent No.: US 6,596,309 B2
(45) Date of Patent: Jul. 22, 2003

(54) STABLE PHARMACEUTICAL DOSAGE FORM FOR PAROXETIN ANHYDRATE

(75) Inventors: Heinz Einig, Neustadt/weinstrasse (DE); Gerhard Fischer, Eberbach (DE); Alfred Reidelshoefer, Michelstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/949,899

(22) Filed: Sep. 12, 2001

(65) Prior Publication Data

US 2002/0058063 A1 May 16, 2002

Related U.S. Application Data

(63) Continuation-in-part of application No. PCT/EP00/02120, filed on Mar. 10, 2000.

(30) Foreign Application Priority Data

Mar. 12, 1999 (DE) .......................... 199 10 954

(51) Int. Cl.⁷ .............................. A61K 9/64; A61K 9/66
(52) U.S. Cl. ...................... 424/456; 424/405; 424/408; 424/451; 424/452; 424/455; 424/486
(58) Field of Search ................ 424/451, 452, 424/405, 408, 455

(56) References Cited

U.S. PATENT DOCUMENTS 4,910,021 A * 3/1990 Davis et al. ................ 424/456
5,413,793 A * 5/1995 Morton et al. .............. 464/436
5,776,969 A 7/1998 James
5,872,132 A 2/1999 Ward et al.

FOREIGN PATENT DOCUMENTS

| | | | |
|---|---|---|---|
| EP | 0 223 403 B1 | 8/1993 | |
| EP | 0 714 663 A2 | 6/1996 | |
| FR | 2624012 | * 12/1987 | ......... A61K/31/045 |
| GB | 2 303 303 A | 2/1997 | |
| WO | WO 95/15155 | 6/1995 | |
| WO | WO 96/31197 | 10/1996 | |
| WO | WO 96/41633 | 12/1996 | |
| WO | WO 97/03670 | 2/1997 | |
| WO | WO 97/31629 | 9/1997 | |
| WO | WO 98/11897 | 3/1998 | |
| WO | WO 98/29136 | 7/1998 | |
| WO | WO 98/31365 | 7/1998 | |
| WO | WO 98/44924 | 10/1998 | |
| WO | WO 99/00131 | * 1/1999 | ......... A61K/31/445 |
| WO | WO 99/26625 | 6/1999 | |
| WO | WO 99/58116 | 11/1999 | |

* cited by examiner

Primary Examiner—Thurman K. Page
Assistant Examiner—Micah-Paul Young
(74) Attorney, Agent, or Firm—Jacobson Holman PLLC

(57) ABSTRACT

Medicaments in the form of soft gelatin capsules contain paroxetin anhydrate or pharmaceutically acceptable salts thereof together with lipophilic carriers, namely silicone oils.

8 Claims, No Drawings

STABLE PHARMACEUTICAL DOSAGE FORM FOR PAROXETIN ANHYDRATE

This is a continuation in part of PCT/EP00/02120, filed Mar. 10, 2000, the disclosure of which is incorporated by reference, herein.

Paroxetin, (—)-trans-4-(4'-fluorophenyl)-3-(3',4'-methylenedioxyphenoxymethyl)-piperidine is described in U.S. Pat. No. 3,912,743 and U.S. Pat. No. 4,007,196 and is employed as an antidepressant. The usual form in which it is administered is the hydrochloride. For general pharmaceutical use and for the formulation of medicaments, the hemihydrate ($\frac{1}{2}H_2O$) is the usual form.

EP-B-0 223 403 describes both the anhydrate and the hemihydrate. Also known are organic solvates, especially with 2-propanol, as described in WO-A-96/24595.

The above mentioned EP-B-0 223 403-describes the preparation of the anhydrate by sharply drying the hemihydrate; however, rehydratation to the hemihydrate occurs very quickly.

WO-A-98/31365 describes the preparation of a free-flowing and easily soluble form as a hemihydrate or solvate. The preparation of a taste-protected paroxetin according to WO-A-95/15155 is based on the use of a complex of the free bases with a copolymer of methacrylic acid and methyl methacrylic acid.

The preparation of a slow-release form is described in WO-A-96/31197 which refers to the use of paroxetin hydrochloride. A concrete example of paroxetin is not stated, but due to the auxiliaries employed for retardation which already contain a considerable amount of water and due to the melting process employed, only the hemihydrate or a higher hydrate can be formed according to the method described therein, even when the paroxetin hydrochloride anhydrate is employed.

Combinations of 5-hydroxytryptamine (5HT) uptake inhibitors (paroxetin, inter alia) with other active ingredients for achieving specific pharmacological and therapeutical effects are described in WO-A-96/41633, GB-A-2 303 303, WO-A-97/31629, U.S. Pat. No. 5,776,969, WO-A-98/44924, EP-A-0 714 663 and WO-A-98/11897. The application examples stated and the non-anhydrous preparations described indicate the use or the subsequent formation of paroxetin hemihydrate.

WO-A-97/03670 describes a slow-release form of paroxetin wherein the use of the free base or the hemihydrate is explicitly mentioned.

From U.S. Pat. No. 5,872,132, four different forms of paroxetin hydrochloride anhydrate are known, of which only form C is claimed. Further, in column 7, lines 9–39, there is described in a general form how oral dosage forms can be prepared from this form.

WO-A-99/00131, which is not a prior published document, describes soft gelatin capsules containing paroxetin as a water-soluble solid dispersion.

However, to date, no medicaments have been known which contain paroxetin or its pharmaceutically acceptable salts as the anhydrate. This is probably due to the fact that these forms of the anhydrate take up water and reform the hemihydrate already during the processing and packaging.

Surprisingly, it has now been found that it is possible to incorporate paroxetin anhydrate or a pharmaceutically acceptable salt thereof in a stable form, without conversion to the hemihydrate, into a medicament if the active ingredient is employed together with lipophilic carriers, namely silicone oils. As acceptable salts, there may be used, for example, the sulfate, methylsulfate, phosphate or carbonate. The preferably employed pharmaceutically acceptable salt is paroxetin hydrochloride anhydrate.

Preferably, the carriers are semisolid or liquid at room temperature.

The medicament according to the invention is in the form of soft gelatin capsules.

The incorporation of paroxetin anhydrate into soft gelatin capsules was surprising because soft gelatin contains very large amounts of water during the encapsulation process. However, it was checked by experiments that a conversion to the hemihydrate did not occur. However, the use of glycerol in the preparation of the capsule coat should be avoided.

A test for absence of the hemihydrate can be performed very simply by infrared spectroscopy or differential scanning calorimetry (DSC), as described by P.C. Baxter et al. in the International Journal of Pharmaceutics, 42 (1988), pages 135 to 143.

The invention also relates to a method for the preparation of the medicament according to the invention wherein paroxetin anhydrate or a pharmaceutically acceptable salt thereof is suspended in lipophilic carriers, namely silicone oils, and the suspension is filled into soft gelatin capsules.

The following Example is intended to further illustrate the invention.

Soft gelatin capsules

In the cold, a mixture is prepared from

| silicone oil, low viscosity | 99.7% |
|---|---|
| silicic acid, highly dispersed | 0.3%. |

Per 207.2 mg of the total mixture, 22.8 mg of paroxetin hydrochloride anhydrate is added. Then, the final mixture is further processed in the known way into soft gelatin capsules. Conveniently, no glycerol is added to the capsule coat.

What is claimed is:

1. A method for the preparation of a medicament characterized in that paroxetin anhydrate or a pharmaceutically acceptable salt thereof is suspended in lipophilic carriers, wherein said lipophilic carriers are silicone oils, and the suspension is filled into soft gelatin capsules to produce a medicament containing the paroxetin anhydrate or pharmaceutically acceptable salts thereof together with the lipophilic carriers in the form of a soft gelatin capsule.

2. The method according to claim 1, characterized in that highly disperse silica is admixed with said silicone oil.

3. The method of claim 1, characterized in that the paroxetin anhydrate or a pharmaceutically acceptable salt thereof is paroxetin hydrochloride anhydrate.

4. The method of claim 3, characterized in that highly disperse silica is admixed with said silicone oil.

5. The method of claim 1, characterized in that said carriers are semisolid or liquid at room temperature.

6. The method of claim 5, characterized in that highly disperse silica is admixed with said silicone oil.

7. The method of claim 3, characterized in that said carriers are semisolid or liquid at room temperature.

8. The method of claim 7, characterized in that highly disperse silica is admixed with said silicone oil.

* * * * *